United States Patent [19]

Ikeda et al.

[11] Patent Number: 5,055,601

[45] Date of Patent: * Oct. 8, 1991

[54] FLUOROEPOXIDES AND A PROCESS FOR PRODUCTION THEREOF

[75] Inventors: Masanori Ikeda, Shizuoka; Morikazu Miura; Atsushi Aoshima, both of Kanagawa, all of Japan

[73] Assignee: Asahi Kasei Kogyo K.K., Tokyo, Japan

[*] Notice: The portion of the term of this patent subsequent to May 15, 2007 has been disclaimed.

[21] Appl. No.: 442,373

[22] Filed: Nov. 28, 1989

Related U.S. Application Data

[60] Division of Ser. No. 69,745, Jul. 6, 1987, Pat. No. 4,965,379, which is a continuation of Ser. No. 517,534, Jul. 26, 1983, abandoned, which is a continuation-in-part of Ser. No. 375,632, May 6, 1982, abandoned.

[30] Foreign Application Priority Data

Jul. 26, 1982 [JP] Japan .................................. 57-129879
Dec. 15, 1982 [JP] Japan .................................. 57-219469

[51] Int. Cl.[5] .......................... C07D 301/29; 301/24
[52] U.S. Cl. ..................................... 549/521; 549/520
[58] Field of Search ............................... 549/520, 521

[56] References Cited

U.S. PATENT DOCUMENTS

| | | | |
|---|---|---|---|
| 3,313,829 | 4/1967 | Rosenblatt ........................ | 549/520 |
| 3,996,259 | 12/1976 | Lee et al. ........................ | 260/465 B |
| 4,006,169 | 2/1977 | Anderson et al. ................. | 549/520 |
| 4,098,834 | 7/1978 | Marsh ................................. | 260/646 |
| 4,925,961 | 5/1990 | Ikeda et al. ........................ | 549/521 |

OTHER PUBLICATIONS

Kelly et al., *Polymer*, "Linear Polymers and Block Copolymers as Solid-Liquid Phase-Transfer Catalysts", 20, pp. 1048-1050 (1979).

I. P. Kolenko et al., *Izv Akad. Nauk SSSR, Ser. Khim.*, (Eng. Trans.), "Fluoro-olefin Oxides", No. 11, pp. 2509-2512 (1979).

*Chemical Abstracts* 92:65502k, Toke, L., "Polyethylene Glycol Derivatives as Complexing Agents and Phase-Transfer Catalysts", (1980).

*Chemical Abstracts*, 95:60668v, Koch, H., "Introduction by Experiments to Phase-Transfer Catalysts", (1981).

Gokel, *J. Chem. Ed.*, 55(6), "Phase Transfer Catalysis", pp. 350-354 (1978).

W. Webber et al., *J. Chem. Ed.*, 55(7), "Phase Transfer Catalysts", pp. 429-433 (1978).

J. McIntosh, *J. Chem. Ed.*, 55(4), "Phase Transfer Catalysis Using Quaternary Onium Salts", pp. 235-238 (1978).

C. M. Starks, "Phase Transfer Catalysts", Academic Press, pp. 112-125 (1979).

*Primary Examiner*—Richard L. Raymond
*Assistant Examiner*—Mark W. Russell
*Attorney, Agent, or Firm*—Sughrue, Mion, Zinn, Macpeak & Seas

[57] ABSTRACT

A process for epoxidation of a fluoro-olefin is disclosed. The process comprises epoxidizing a fluoro-olefin represented by the general formula (I):

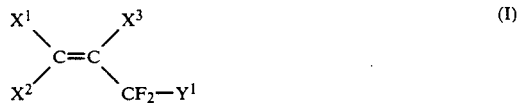

wherein $X^1$, $X^2$ and $X^3$ each represents a substituent selected from (a)—F, (b) a perfluoroalkyl group having 2 to 20 carbon atoms and (c) —$CF_2Y^1$, $Y^1$ may be the same or different and represents a substituent selected from (d) a halogen atom selected from F, Cl, Br and I, (e) —$OZ^1$ and (f) —$Z^1$, wherein $Z^1$ may be the same or different and represents a substituted or unsubstituted hydrocarbon group having not more than 20 carbon atoms, and $X^1$, $X^2$, $X^3$ and $Y^1$ may be combined with one another to form a cyclic compound, provided that all of $X^1$, $X^2$, $X^3$ and $Y^1$ do not represent —F; using a hypochlorite dissolved or suspended in an aqueous phase as an oxidizing agent in the presence or absence of an inorganic base. The reaction is performed in a two phase system (aqueous and organic phases) in the presence of at least one phase transfer catalyst selected from (i) quaternary ammonium salts, (ii) quaternary phosphonium salts, (iii) quaternary arsonium salts, (iv) sulfonium salts and (v) lipophilic complexing agents for cations contained in the hypochlorite.

34 Claims, No Drawings

FLUOROEPOXIDES AND A PROCESS FOR PRODUCTION THEREOF

CROSS REFERENCES

This is a divisional of parent application Ser. No. 07/069,745, filed July 6, 1987 now U.S. Pat. No. 4,465,379, which is a continuation of grandparent application Ser. No. 06/517,534, filed July 26, 1983 now abandoned, which is a Continuation-in-Part of great grandparent application Ser. No. 06/375,632, filed May 6, 1982 now abandoned.

FIELD OF THE INVENTION

The present invention relates to fluoroepoxides and a process for production of fluoroepoxides and, more particularly to a process for epoxidation of fluoro-olefins by a simplified procedure and in high yields.

BACKGROUND OF THE INVENTION

In general, fluoroepoxides can be prepared by epoxidation of fluoro-olefins. Due to the fact that fluoro-olefins have chemical properties very different from hydrocarbon-type lefins such as propylene or chlorinated hydrocarbon-type olefins such as allyl chloride, however, it is difficult to epoxidize fluoro-olefins in a manner similar to propylene or allyl chloride.

For example, both propylene and allyl chloride are epoxidized by a chlorohydrin process which effects cyclization with an alkali via chlorohydrin. On the other hand, in the epoxidation of fluoro-olefins by the chlorohydrin process, chlorohydrin is unstable and decomposes to carbonyl compounds so that it is impossible to change it into fluoroepoxides.

Accordingly, a variety of processes have heretofore been proposed for epoxidation of fluoro-olefins which are different from the process for the epoxidation of hydrocarbon-type olefins or chlorinated hydrocarbon-type olefins. However, none of these processes are industrially advantageous processes for preparing fluoroepoxides.

A process as described in U.S. Pat. No. 3,358,003 which comprises oxidizing fluoro-olefins to fluoroepoxides in an alkaline hydrogen peroxide medium, a process as described in U.S. Pat. No. 3,536,733 which comprises oxidizing fluoro-olefins to fluoroepoxides with oxygen in the presence of an inert solvent, etc. are heretofore known as typical processes for preparing fluoroepoxides. However, it is impossible to obtain fluoroepoxides in high yield since, in any of these processes, it is difficult to control the reaction, it is difficult to prevent the decomposition of the formed fluoroepoxides, or large quantities of side-products are by-produced, etc. Further, a high conversion of fluoro-olefins results in reduction in selectivity of fluoroepoxides. In order to effectively use fluoro-olefins, it is thus necessary to discontinue the reaction at a low fluoro-olefin conversion, separate the unreacted fluoro-olefins from fluoroepoxides, recover and re-use them. However, the boiling points of fluoro-olefins are generally very close to those of fluoroepoxides so that it is difficult to separate both from each other through distillation, and special procedures are thus required for the separation. As typical examples for such procedures, a method which comprises reacting the unreacted fluoro-olefins with bromine to convert them into dibromo-compounds having high boiling point and then separating the dibromo-compounds from fluoroepoxides, and methods for separation through extracive distillation as described in U.S. Pat. Nos. 3,326,780 and 4,134,796 have been proposed. However, these methods are complicated and seriously increase the production costs of fluoroepoxides.

On the other hand, it is known in a process comprising oxidation using hypochlorites that fluoroepoxides are produced from fluoro-olefins in a system where a polar solvent such as acetonitrile, diglime, etc., is incorporated into a hypochlorite aqueous solution (*IZV. AKAD. NAUK. SSSR, SER. KHIM.*, 79 (11) 2509). The study of this process by the present inventors revealed that the selectivity of fluoroepoxides was poor and fluoroepoxides could not be obtained in high yield. Although it is not completely understood, it is assumed that the formed fluoroepoxides would easily react with water and decompose under alkaline conditions since the reaction system is a homogeneously mixed system of a polar solvent and an alkaline hypochlorite aqueous solution. In addition, a complicated step of recovering the polar solvent from the reaction system after completion of the reaction is also required in this process. In view of the foregoing, it can be understood that the process of this reaction type cannot be used as a practical technique for the preparation of fluoroepoxides.

As a result of extensive investigations attempting to overcome such drawbacks in the prior art processes and find a process for preparing fluoroepoxides in a simple manner and high yield, the present inventors have found that when the reaction is carried out in a two phase system of an aqueous phase and an organic phase using hypochlorites as oxidizing agents in the presence of at least one phase transfer catalyst selected from the group consisting of quaternary ammonium salts, quaternary phosphonium salts, quaternary arsonium salts, sulfonium salts and lipophilic complexing agents for cations contained in hypochlorites, fluoroepoxides are obtained from fluoro-olefins in high yields.

SUMMARY OF THE INVENTION

The present invention provides a novel process for the epoxidation of fluoro-olefins which comprises epoxidizing fluoro-olefins represented by the general formula (I):

wherein $X^1$, $X^2$ and $X^3$ each represents a substituent selected from (a) —F, (b) a perfluoroalkyl group having 2 to 20 carbon atoms and (c) —$CF_2Y^1$, $Y^1$ may be the same or different and represents a substituent selected from (d) a halogen atom selected from F, Cl, Br and I, (e) —$OZ^1$ and (f) —$Z^1$, wherein $Z^1$ may be the same or different and represents a substituted or unsubstituted hydrocarbon group having carbon atoms of not greater than 20, and $X^1$, $X^2$, $X^3$ and $Y^1$ may be combined with one another to form a cyclic compound, provided that all of $X^1$, $X^2$, $X^3$ and $Y^1$ do not simultaneously represent —F; in a two-phase system of an aqueous phase and an organic phase using a hypochlorite dissolved or suspended in the aqueous phase as an oxidizing agent in the presence of at least one phase transfer catalyst selected from (i) quaternary ammonium salts, (ii) quaternary phosphonium salts, (iii) quaternary arsonium salts, (iv) sulfonium salts and (v) lipophilic complexing agents for cations contained in hypochlorites. (Hereafter, the fluoro-olefins represented by the general formula (I) are simply referred to as "fluoro-olefins" and the resulting fluoroepoxides are simply referred to as "fluoroepoxides".

The fluoroepoxides are very reactive and important as intermediates for a variety of fluorine compounds. The fluoroepoxides are also important substances that can per se be raw materials for high molecular weight substances.

DETAILED DESCRIPTION OF THE INVENTION

In the two phase system reaction of the present invention, substantially all of the fluoro-olefins and the formed fluoroepoxides are contained in the organic phase. According to the process of the present invention, the fluoroepoxides are obtained in high selectivity even though the conversion of the fluoro-olefins is high. This is assumed to be because the decomposition of fluoroepoxides due to contact with an alkaline aqueous solution would occur only with difficulty since the formed fluoroepoxides are present in the phase different from the phase where the alkaline aqueous solution is present. According, it is also possible to eliminate a complicated step of separating the fluoro-olefins and the fluoroepoxides and a step of recycling the unreacted fluoro-olefins.

After completion of the reaction, the organic phase is separated from the aqueous phase. The fluoroepoxides are easily isolated from the organic phase by means of operations for separation such as distillation or the like. Further, the catalyst is contained in the residual organic phase from which the fluoroepoxides has been removed. The residual organic phase can be recycled and re-used in the reaction as is, so that the recovery of the solvent and the catalyst is very simply effected.

As described above, the fluoroepoxides can be obtained in high yield and the production steps become very simple in the process of the present invention. Accordingly, construction costs of reaction equipments and running costs become inexpensive in the practice of the process in accordance with the present invention. Accordingly, the present invention can provide a very economical process for preparation of the fluoroepoxides.

Hereafter the present invention will be described in more detail.

The present invention makes use of fluoro-olefins represented by the general formula (I):

wherein $X^1$, $X^2$ and $X^3$ each represents a substituent selected from (a) —F, (b) a perfluoroalkyl group having 2 to 20 carbon atoms and (c) —$CF_2Y^1$; $Y^1$ may be the same or different and represents a substituent selected from (d) a halogen atom selected from F, Cl, Br and I, (e) —$OZ^1$ and (f) —$Z^1$, wherein $Z^1$ may be the same or different and represents a substituted or unsubstituted hydrocarbon group having carbon atoms of not greater than 20; and $X^1$, $X^2$, $X^3$ and $Y^1$ may combine with one another to form a cyclic compound; provided that all of $X^1$, $X^2$, $X^3$ and $Y^1$ do not simultaneously represent —F.

The substituted or unsubstituted hydrocarbon group $Z^1$ contained in the general formular (I) are not overly limited but various substituted or unsubstituted hydrocarbon groups are usable as long as they can be stably present under the alkaline condition in the process of the present invention and in the presence of hypochlorites, or do not prevent the reaction of the present invention even though they are modified under the reaction conditions of the present invention. Examples of hydrocarbon groups which are valuable in a practical sence include hydrocarbon groups, such as an alkyl group, an alkenyl group, an aryl group, an aralkyl group, etc., having carbon atoms of not greater than 20, preferably 14 or less, more preferably 8 or less, which may be substituted with a substituent such as a halogen atom, an ether group, a nitrile group, etc.

Further, the carbon atom number of the perfluoroalkyl group contained in the fluoro-olefins is not particularly limited but is generally within the range of 2 to 20, preferably the range of 2 to 14 and most preferably the range of 2 to 8.

Specific examples of the fluoro-olefins which can be used in the process of this invention include perfluoro-olefins such as perfluoro-2-butene, perfluoro-1-butene, perfluoro-2-pentene, perfluoro-1-hexene, perfluoro-2-hexene, perfluoroheptene-1, perfluorononene-1, perfluorodecene-1, perfluorooctadecene-1, perfluoro-4-methylpentene-2, perfluoro-4-methylpentene-3, perfluoro-4,6-dimethylheptene-4, perfluoro-2-methyl-3-isopropylpentene-3, perfluorocyclopentene, perfluorocyclohexene, etc.; chlorofluoro-olefins such as 4,5-dichloroperfluoro-1-pentene, 5,6-dichloroperfluoro-1-hexene, 6,7-dichloroperfluoro-1-heptene, 9,10-dichloroperfluoro-1-decene, 4,6,7-trichloroperfluoro-1-heptene, 3-chloropentafluoropropene, etc.; bromofluoro-olefins such as 4-bromoperfluoro-butene-1,5,6-dibromoperfluoro-1-hexene, 3-bromopentafluoropropene, etc.; iodofluoro-olefins such as 4-iodoperfluorobutene-1,3-iodopentafluoropropene, etc.; nitril group-containing fluoro-olefins such as heptafluoro-4-pentenenitrile, etc.; perfluorodienes such as perfluoro-1,5-hexadiene, perfluoro-1,7-octadiene, etc.; ω-hydroperfluoro-olefins such as ω-hydroperfluorohexene-1,ω-hydroperfluorooctene-1, etc.; polyfluoro-olefins such as 1,1,2,3,3-pentafluoro-1-butene, etc.; polyfluorodienes having both perfluoroallyl group and vinyl group; fluoro-olefins containing various fluoroalkoxy groups such as a perfluoro-n-propoxy group, a perfluoro-i-propoxy group, a perfluoroalkoxy group derived from oligomers of hexafluoropropylene oxide, or a nitrile-containing fluoroalkoxy group and the like (e.g., perfluoro-5-trifluoromethyl-4-oxahexene-1); fluoro-olefins containing a perfluorovinyloxy group such as 4-perfluorovinyloxyperfluoro-1-butene, etc. Of these fluoro-olefins, di- or multi-functional fluoro-olefins such as chlorofluoro-olefins, bromofluoro-olefins, iodofluoro-olefins, perfluorodienes, perfluoroalkoxy-olefins and perfluorovinyloxy-olefins are particularly preferred since each functional site can be used for different function, for example, one functional site for the reaction and the other for the revelation of the nature of the material, or two different functional sites for the different reactions, to form highly valuable materials. Most of the epoxides of these di- or multi-functional fluoro-olefins are not very stable and have now come to be obtained in practical yields for the first time by means of the present epoxidation method under mild reaction conditions.

The fluoroepoxides synthesized from the fluoro-olefins by the process of the present invention are very reactive and can easily be derived to a variety of useful fluorine-containing compounds. For example, fluorine-containing carbonyl compounds which are important intermediates for synthesis and perfluorovinyl ethers which are raw materials for preparing ion exchange resins or fluororesins can easily be synthesized from the fluoroepoxides. In addition, the fluoroepoxides per se are important substances which can be raw materials for preparing fluorine-containing high molecular weight compounds. Further, oligomers of the fluoroepoxides can also be employed as raw materials for fluorine-containing surface active agents or fluorine-containing lubricants.

In particular, the fluoroepoxides having the following structures,

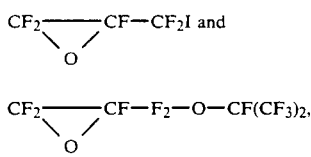

are very important new fluoroepoxides which are synthesized by the process of the present invention for the first time. It is surprising that such a polyfunctional fluoroepoxide can be synthesized in a high yield. Presently, only a process for the synthesis of

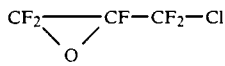

which comprises oxidizing $CF_2=CF-CF_2Cl$ with oxygen has be reported in U.S. Pat. No. 3,536,744 (Oct. 27, 1970) as a process for synthesis of

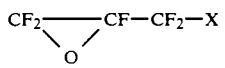

wherein X represents a halogen atom other than F. It is assumed that various

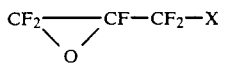

type compounds could be synthesized through oxidation of $CF_2=CF-CF_2-X$. However, when X represents Br or I, particularly I, the $-CF_2-X$ groups are susceptible to decompose by heat, light or radical species and easily decompose under the reaction conditions in conventional oxidation. It is thus difficult to obtain such a compound in a practical yield in conventional processes for oxidation. However, the process of the present invention has for the first time made it possible to synthesize

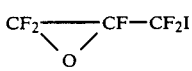

by the use of the oxidation under very mild reaction conditions.

The compound, $CF_2=CFCF_2I$, which is a raw material for the synthesis of

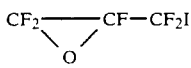

can easily be synthesized by, for example, the reaction (1) shown in *J. Amer. Chem. Soc.*, 103, 5598 (1981), or the reaction (2) shown in *J. Amer. Chem. Soc.*, 79, 4164 (1957).

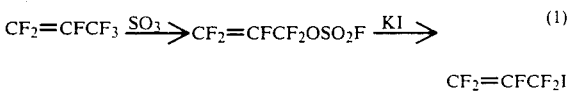

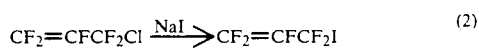

As described above, the compound,

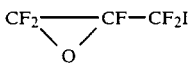

is a bifunctional compound containing the very reactive perfluoroepoxy ring and the $-CF_2I$ group therein, and by utilizing the reactivities of the two functional groups a variety of useful compounds can be prepared therefrom. As is described in, e.g. *Yuki Gosei Kagaku (Organic Synthetic Chemistry)*, 35, 131 (1977), the perfluoroepoxy ring is easily isomerized by a basic catalyst to convert into various carbonyl compounds, as shown in the equations (3) and (3')

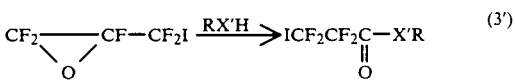

wherein R represents an alkyl group, etc. and X' represents O, S or NH. Further, the perfluoroepoxy ring is easily opened by the attack of various nucleophilic reagents to form addition products. Therefore, the utilization of such a reactivity of the perfluoroepoxy ring results in useful synthetic intermediates containing an active $-CF_2I$ group.

The $-CF_2I$ group in the thus prepared synthetic intermediates is a very reactive substituent and can be utilized for, e.g., reactions described below.

(i) *Chemistry of Organic Fluorine Compounds*, 2nd, ed., John Wiley & Sons, New York, pages 20 and 21

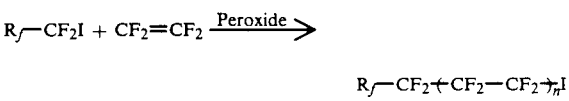

(ii) *J. Org. Chem.*, 36, 364 (1971)

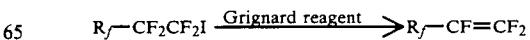

(iii) *J. Amer. Chem. Soc.*, 75 5750 (1953); ibid., 72 4809 (1950)

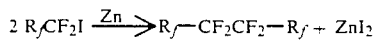
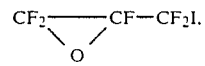

On the other hand, the —CF$_2$Cl group or the —CF$_2$Br group is stable as compared to the —CF$_2$I group due to a large binding energy in the C—X is utilized, however, CF$_2$=CFOCF$_2$CF$_2$CF$_2$I can easily be synthesized by the following process.

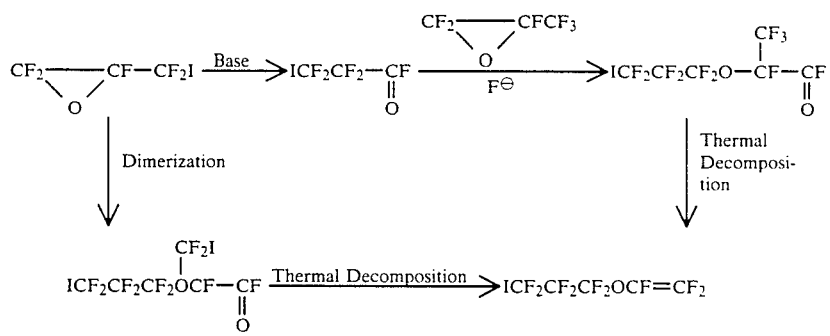

(wherein X is Cl, Br or I) bond so that the aforesaid reactions occur only with extreme difficulty. Accordingly, the reactions described above are characteristic of compounds containing the —CF$_2$I group.

The utilization of the bifunctionality of

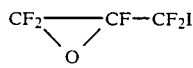

results in easy synthesis of various fluorine-containing compounds which have been heretofore synthesized only with difficulty. As an example, functional monomers (cross-linking site monomers) such as CF$_2$=CFOCF$_2$CF$_2$CF$_2$I containing the reactive —CF$_2$I group, which is described in French Patent 1,410,444, can be easily synthesized using

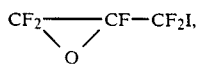

while it is difficult to synthesize by a prior art technique.

More specifically, while in French Patent 1,410,444 various compounds represented by the formula

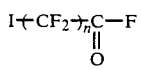

are used for synthesis of I—CF$_2$)$_{n+1}$OCF=CF$_2$, the compounds,

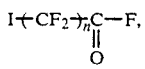

are synthesized via a process using tetrafluoroethylene oxide which is synthesized only with difficulty, unstable and dangerous, or a process which comprises reacting I—CF$_2$)$_n$CF$_2$I and SO$_3$ involving difficulty in reaction and poor yield.

Therefore, any process shown above cannot be advantageous from an economical viewpoint. When the compound, Further when utilizing the reactivity of the —CF$_2$I group, it becomes possible to synthesize functional perfluorovinyl ethers useful as raw materials of ion exchange resins in high selectivity under mild reaction conditions as will be later described. In addition, by the utilization of the oligomerization of tetrafluoroethylene etc. using the —CF$_2$I group as a telogen, polar compounds containing long chain perfluoroalkyl groups useful as surface active agents or surface modifiers can be easily synthesized.

In Japanese Patent Application (OPI) No. 28024/82 (U.S. patent application Ser. No. 158,427 filed in 1980), a process for preparing functional perfluorovinyl ethers represented by formula (IV) which are useful as raw materials for preparing ion exchange membranes is shown:

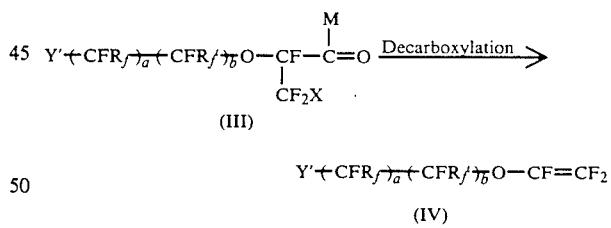

wherein X represents Cl, I or Br; Y' represents an acid derivative group; R$_f$ and R$_f'$ each represents a group selected from the group consisting of F, Cl, a perfluoroalkyl group and a fluorochloroalkyl group; a represents 0 to 3; b represents 0 to 3; a+b represents 2 or 3; M represents OR', F, Cl, Br, I or OA; A represents an alkali metal, an alkaline earth metal, a quaternary nitrogen or hydrogen; R' is an alkyl group having 1 or more carbon atoms or an aryl group).

Of the raw compounds represented by the formula (III), a compound wherein X represents I is most reactive, and when using this compound, the reaction proceeds under mild reaction conditions to obtain a high selectivity. However, it is extremely difficult to synthesize the compound (III) (wherein X represents I) by the prior art technique. When using the novel compound

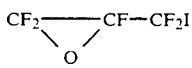

in accordance with the present invention, however, the compound (III) (wherein X represents I) can easily be synthesized by the reaction shown by the equation (4):

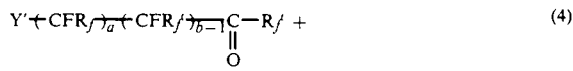 (4)

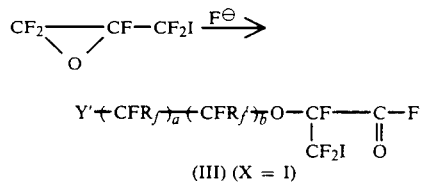

(III) (X = I)

The compound,

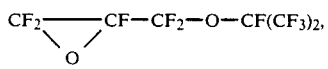

is also a useful, novel fluoroepoxide which has been first synthesized by the process of the present invention. The compound can be synthesized from a compound having the structure $CF_2=CF-CF_2-O-CF(CF_3)_2$ by the epoxidation of the present invention. The compound, $CF_2=CF-CF_2-O-CF(CF_3)_2$, can easily be prepared, e.g., by the following process:

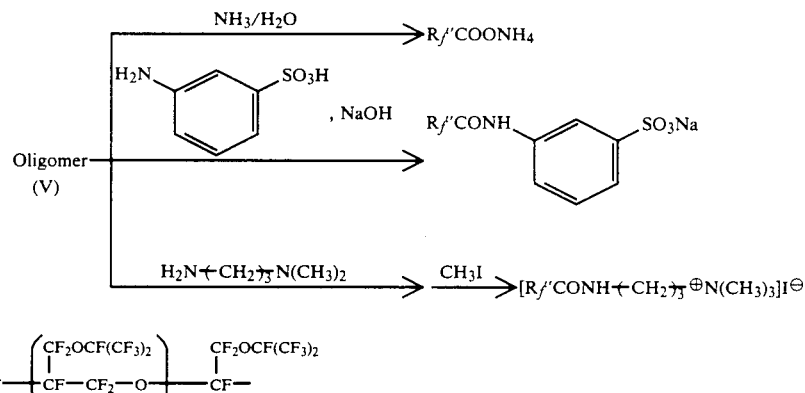

The compound,

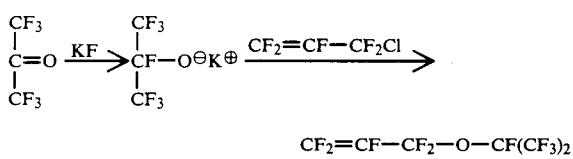

is a reactive substance which contains the $-CF(CF_3)_2$ group showing a very low surface energy. Thus, by utilizing the reactivity of the perfluoroepoxy ring, various high performance fluorinated surface active agents or surface modifiers can be synthesized. For example, oligomers of

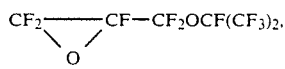

which are represented by the general formula (V), are reactive substances containing the $-CF(CF_3)_2$ group showing a low surface energy in a predominant proportion.

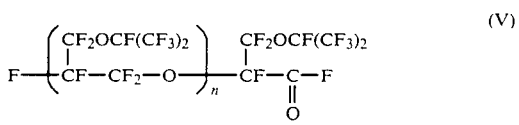 (V)

Therefore, the oligomers (V) per se are useful as reactive surface modifiers. Further, various high performance surface active substances can be synthesized by reactions indicated below in a manner similar to those described in *Preliminary Report of the* 6th Fluorine Chemistry Forum, page 21 (1980).

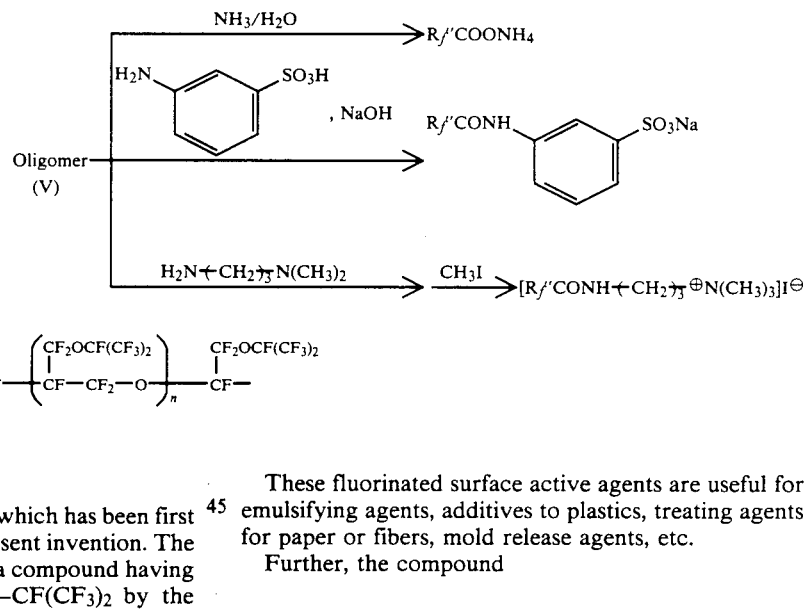

These fluorinated surface active agents are useful for emulsifying agents, additives to plastics, treating agents for paper or fibers, mold release agents, etc.

Further, the compound

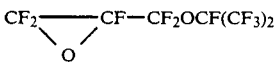

per se is useful as a surface modifier for materials having various active hydrogens at the surface thereof, utilizing the reactivity of the perfluoroepoxy ring.

Turning next to hypochlorites which can be used as an oxidizing agent in the present invention, typical examples include alkali metal salts such as lithium hypochlorite, sodium hypochlorite, potassium hypochlorite, rubidium hypochlorite, cesium hypochlorite, etc.; alkaline earth metal salts such as magnesium hypochlorite, calcium hypochlorite, strontium hypochlorite, barium hypochlorite, etc. Of these hypochlorites, sodium hypochlorite and calcium hypochlorite are particularly suited as the hypochlorites used in the process of the present invention since these hypochlorites are mass produced in an industrial scale for use as bleaching agents, sterilizers, etc. Further, they are inexpensive and easily accessible. Commercially available hypochlorites can be used as they are or, those prepared from inorganic bases and chlorine gas or those prepared by non-membrane electrolysis of inorganic chlorides may also be used.

The hypochlorites as used herein is dissolved mainly in an aqueous phase, and the concentration of the hypochlorite is not particularly limited. It is generally desired that the available chlorine content be in the range of 0.5 to 25% by weight, preferably in the range of 1 to 20% by weight. When the available chlorine content is too low, a large amount of the aqueous phase must be handled and such is disadvantageous from an economical viewpoint. Further, when the available chlorine content is too high, the hypochlorite becomes unstable, which renders the handling difficult.

The ratio of the hypochlorite to the fluoro-olefin can be freely chosen but for obtaining substantial reaction results, the ratio is chosen from the range of 0.5 to 30 gram equivalents, preferably from the range of 0.8 to 10 gram equivalents, more preferably from the range of 1 to 10 gram equivalents as hypochlorite ions based on 1 mol of the fluoro-olefin.

The process of the present invention can be practiced in the presence or absence of inorganic bases. It is preferred to carry out the reaction in the presence of inorganic bases because of the following advantages. A first effect achieved by the presence of the inorganic bases is to obtain high selectivity of the fluoroepoxide even when the conversion of the fluoro-olefin is increased. Accordingly, the conversion of the fluoro-olefin can be increased without seriously damaging the selectivity of the fluoroepoxide and the amount of the remaining fluoro-olefin can be minimized. Accordingly, the fluoroepoxide having high purity can be obtained in high yield without any step of separating the fluoroepoxide. A second effect is to obtain good results even though the ratio of the hypochlorite to the fluoro-olefin is decreased. In the absence of the inorganic bases or in the presence of a small quantity of the inorganic bases, when the ratio of the hypochlorite to the fluoro-olefin is low, the selectivity of the fluoroepoxide is reduced, and the residual available chlorine content is reduced in the course of the reaction. This leads to no further increase in the fluoro-olefin conversion. It is thus necessary that the reaction be carried out in the presence of a large excess of hypochlorites in order to obtain good results. When the process of the present invention is carried out in the presence of more than a specific amount of the inorganic bases, however, the amount of the hypochlorite to be used can be reduced so that it becomes possible to minimize costs of the hypochlorite, reduce the size of reaction equipments involved and minimize costs of waste water treatment.

Typical examples of the inorganic bases which can be used in the process of the present invention include alkali metal hydroxides such as lithium hydroxide, sodium hydroxide, potassium hydroxide, rubidium hydroxide, cesium hydroxide, etc.; alkaline earth metal hydroxides such as calcium hydroxide, strontium hydroxide, barium hydroxide, etc. These inorganic bases may be dissolved in the aqueous phase or may not be completely dissolved in the aqueous phase but may be present as a solid phase. Of these various inorganic bases, sodium hydroxide is particularly suited in view of costs, solubility in water, easiness in handling, etc.

The amount of the inorganic base used in the process of the present invention can be freely set forth, but in order to obtain substantial effects, it is generally preferred to use not less than 0.1 gram equivalent based on 1 mol of the fluoro-olefin used in the reaction. The whole amount of the inorganic base may be present in the reaction system from the initial stage of the reaction or, depending upon the situation, may also be incorporated in appropriate amounts during the course of the reaction.

As the catalyst suited for the process of the present invention, so-called phase transfer catalysts are used. Of these, effective catalysts are quaternary ammonium salts, quaternary phosphonium salts, quaternary arsonium salts, sulfonium salts and lipophilic complexing agents for cations contained in the hypochlorites. It is preferred that these catalysts have affinity to the organic phase.

As the quaternary ammonium salts used in the process of the present invention, a variety of quaternary ammonium salts are represented by the general formula (VI):

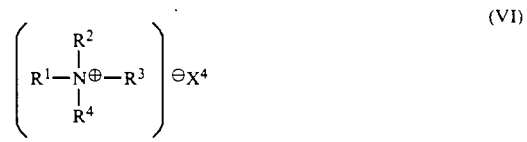

wherein $R^1$, $R^2$, $R^3$ and $R^4$, which may be the same or different from one another, each represents a hydrocarbon group which may be substituted with an inert functional group under the reaction conditions. The kind and length of the hydrocarbon group can be appropriately chosen depending upon the solvent to be used, the reaction rate required, etc. Examples of the hydrocarbon group include an alkyl group, an alkenyl group, a cycloalkyl group, a cycloalkenyl group, an aryl group, an aralkyl group, an alkenylaryl group, etc. Of these, particularly preferred are an alkyl group, an aryl group, an aralkyl group, etc. Further the length of the hydrocarbon group is generally chosen from the range of 6 to 100, preferably from the range of 8 to 70, more preferably from the range of 10 to 50, per one quaternary ammonium ion, as the total carbon atom numbers contained in $R^1$, $R^2$, $R^3$ and $R^4$.

The inert functional group which can be substituted on the aforesaid hydrocarbon group is limited depending upon the reaction condition but generally selected from a halogen atom, an acyl group, a carboxyl group, an ester group, a nitrile group, an alkoxyl group and the like. In the formula (VI), $R^1$ and $R^2$ or $R^1$, $R^2$ and $R^3$ may be combined together to form a nitrogen-containing heterocyclic ring, or $R^1$, $R^2$, $R^3$ or $R^4$ may also take a part of a high molecular weight compound.

Specific examples of quaternary ammonium ions include tetraethyl ammonium ions, tetra-n-propylammonium ions, tetra-n-butylammonium ions, tri-n-octylmethylammonium ions, cetyltrimethylammonium ions, benzyltrimethylammonium ions, benzyltriethylammonium ions, cetylbenzyldimethylammonium ions, cetylpyridinium ions, n-dodecylpyridinium ions, phenyltrimethylammonium ions, phenyltriethylammonium ions, N-benzylpicolinium ions, pentamethonium ions, hexamethonium ions, etc.

The anion $\ominus X^4$ in the formula (VI) is not particularly limited but various anions can be employed. In general, halogen ions, various mineral acid ions other than halogen ions, organic acid ions, hydroxide ions, etc. are employed.

Specific examples of the anion $\ominus X^4$ include chlorine ions, bromine ions, iodine ions, fluorine ions, hydrogen sulfate ions, sulfuric acid ions, nitric acid ions, phosphoric acid ions, perchloric acid ions, hydroxide ions, acetic acid ions, benzoic acid ions, benzenesulfonic acid ions, p-toluenesulfonic acid ions, etc. Of these, particularly preferred are chlorine ions, hydrogen sulfate ions, hydroxide ions.

As the quaternary phosphonium salts which can be used in the process of the present invention, various quaternary phosphonium salts represented by the general formula (VII) are illustrated.

(VII)

wherein $R^5$, $R^6$, $R^7$ and $R^8$, which may be the same or different, each represents a hydrocarbon group which may be substituted with an inert functional group under the reaction condition. The kind and length of the hydrocarbon group are appropriately chosen depending upon the solvent used, the reaction rate required, etc. Typical examples of the hydrocarbon group include an alkyl group, an alkenyl group, a cycloalkyl group, a cycloalkenyl group, an aryl group, an aralkyl group, an alkenylaryl group, etc. with an alkyl group, an aryl group and an aralkyl group being preferred. Further the carbon atom number as the total of the carbons contained in $R^5$, $R^6$, $R^7$ and $R^8$ is generally chosen from the range of 6 to 100, preferably from the range of 8 to 70, more preferably from the range of 10 to 50, per one quaternary phosphonium ion. The inert functional group which can be substituted on the aforesaid hydrocarbon group is limited depending upon the reaction condition but generally selected from a halogen atom, an acyl group, a carboxyl group, an ester group, a nitrile group, an alkoxyl group, etc. In the formula (VII), $R^5$ and $R^6$ or $R^5$, $R^6$ and $R^7$ may be combined with one another to form a heterocyclic ring, or $R^5$, $R^6$, $R^7$ or $R^8$ may constitute a part of a high molecular weight compound.

Specific examples of the quaternary phosphonium ions include tetraethylphosphonium ions, tetra-n-butylphosphonium ions, tri-n-octylethylphosphonium ions, cetyltriethylphosphonium ions, cetyltri-n-butylphosphonium ions, n-butyltriphenylphosphonium ions, n-amyltriphenylphosphonium ions, n-hexyltriphenylphosphonium ions, n-heptyltriphenylphosphonium ions, methyltriphenylphosphonium ions, benzyltriphenylphosphonium ions, tetraphenylphosphonium ions, etc.

The anion $\ominus Y^2$ in the formula (VII) is not particularly limited but various anions can be used. In generaly, halogen ions, various mineral acid ions other than halogen ions, organic acid ions and the like are employed.

Specific examples of the anion $\ominus Y^2$ include chlorine ions, bromine ions, iodine ions, fluorine ions, hydrogen sulfate ions, sulfuric acid ions, nitric acid ions, phosphoric acid ions, perchloric acid ions, p-toluenesulfonic acid ions, etc. Of these, particular preferred are chlorine ions and bromine ions.

Sulfonium salts which can be used in the process of the present invention are represented by the general formula (VIII):

(VIII)

In the general formula (VIII), $R^9$, $R^{10}$ and $R^{11}$, which may be the same or different, each represents a hydrocarbon group or a secondary amino group. The kind and length of the hydrocarbon group or a hydrocarbon group contained in the secondary amino group can be suitably chosen depending upon the solvent used, the reaction rate required, or the like. Specific examples of the hydrocarbon group include an alkyl group, an alkenyl group, a cycloalkyl group, a cycloalkenyl group, an aryl group, an aralkyl group, an alkenylaryl group, etc. Of these, particularly preferred are an alkyl group, an aryl group, an aralkyl group and the like. Further the length of the hydrocarbon group is generally chosen from the range of 6 to 100, preferably from the range of 8 to 90, more preferably from the range of 10 to 80, per one sulfonium ion, as the total carbon atom number contained in $R^9$, $R^{10}$ and $R^{11}$. The aforesaid hydrocarbon group can be substituted with an inert functional group. The inert functional group is limited depending upon the reaction conditions but is generally selected from a halogen atom, an acyl group, a carboxyl group, an ester group, a nitrile group, an alkoxy group, etc. In the $R^9R^{10}R^{11}S^\oplus$ion, a heterocyclic ring may also be formed within the ions, or $R^9$, $R^{10}$ or $R^{11}$ may be a part of a high molecular weight compound.

As the anion $\ominus Z^2$ in the general formular (VIII), various anions can be used but halogen ions, various mineral acid ions other than halogen ions, organic acid ions and the like are generally employed.

Specific examples of the anion $\ominus Z^2$ include chlorine ions, bromine ions, iodine ions, fluorine ions, hydrogen sulfate ions, sulfuric acid ions, nitric acid ions, phosphoric acid ions, perchloric acid ions, p-toluenesulfonic acid ions, tetrafluoroborate ions, difluorotrimethylsilicate ions, etc.

Specific examples of the sulfonium salts represented by the general formula (VIII) include dibutylmethylsulfonium iodide, tri-n-butylsulfonium tetrafluoroborate, dihexylmethylsulfonium iodide, dicyclohexylmethylsulfonium iodide, dodecylethylmethylsulfonium chloride, methyldioctadecylsulfonium iodide, dodecylbenzylmethylsulfonium methylsulfate, 1,6-hexamethylenebis(dimethylsulfonium bromide), tris(dimethylamino)sulfonium difluorotrimethyl silicate, tris(diethylamino)sulfonium difluorotrimethyl silicate, tris(N-methyl-N-octadecylamino)sulfonium difluorotrimethyl silicate, tris(dimethylamino)sulfonium chloride, etc.

As the quaternary arsonium salts which are employed in the process of the present invention, it may be sufficient that the quaternary arsonium ions have affinity to the organic phase and can be present stably under the reaction conditions of the present invention. Specific examples of the arsonium salts include tetraarylarsonium salts and triarylalkylarsonium salts, such as tetraphenylarsonium chloride, triphenylmethylarsonium chloride, tetraphenylarsonium bromide, etc., and high molecular weight derivatives thereof.

The lipophilic complexing agent for cations contained in the hypochlorite (e.g., an alkali metal ion and an alkaline earth metal (excluding beryllium) ion) which is employed in the process of the present invention can be any compound if it has a capability of complexing the cations and affinity to the organic phase. However, it is a matter of course that the complexing agent must take a stable structure under the reaction conditions of the present invention.

As the lipophilic complexing agent used in the process of the present invention, any compound can be used as long as it satisfies the aforesaid requirements and is chosen from a very wide range of compounds. Hereafter examples of the lipophilic complexing agent which can be used in the process of the present invention will be shown but the lipophilic complexing agent is not limited thereto.

(1) Macrocyclic Polyethers

Macrocyclic polyethers are generally called "crown ethers" (see, e.g., Pedersen, *J. Amer. Chem. Soc.*, 89, 2495, 7017 (1967)) and it is known that these polyethers show a strong capability of configuration to alkali metal ions or alkaline earth metal ions. Most of the "crown ethers" are represented by the general formular (IX) or substituted deviatives thereof:

(IX)

wherein n is an integer of from 4 to 20, m is an integer of from 1 to n, and $l_1, l_2, \text{---}$ and $l_n$ which may be the same or different, each is an integer of from 2 to 4.

Specific examples of the crown ethers include 18-crown-6, dicyclohexyl-18-crown-6, dibenzo-18-crown-6, benzo-15-crown-5, dibenzo-15-crown-5, dibenzo-21-crown-7, dibenzo-24-crown-8, dibenzo-30-crown-10, dicyclohexyl-24-crown-8, etc., according to the nomenclature by Pedersen.

(2) Macrocyclic Aminoethers

Examples of macrocyclic amino ethers include bicyclic aminoethers and monocyclic aminoethers.

The bicyclic aminothers are generally termed "cryptand" (e.g., Lehn, *Tetrahedron Lett.*, 2885, 2889 (1969)) and it is known that these aminoethers show a very strong capability for configuration to alkali metal ions or alkaline earth metal ions. Most "cryptand" are represented by the general formula (X) or substituted derivatives thereof:

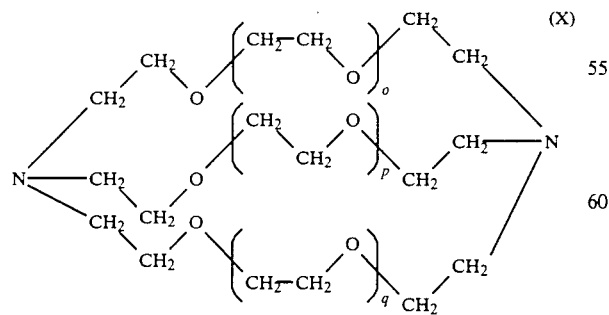
(X)

(o = 0, 1, 2; p = 0, 1, 2; q = 0, 1, 2)

Specific examples include the following compounds:

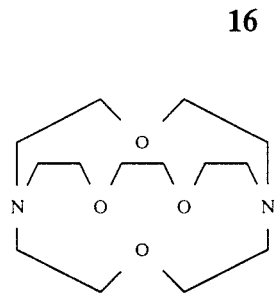
(X-a)

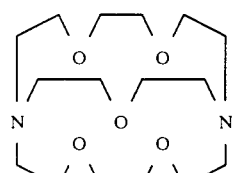
(X-b)

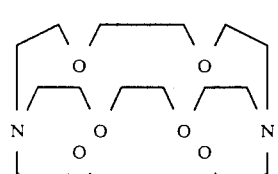
(X-c)

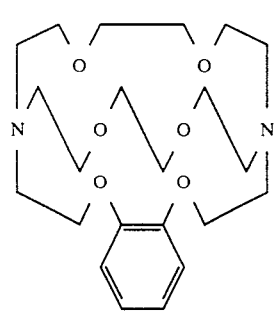
(X-d)

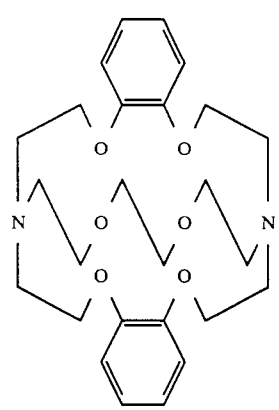
(X-e)

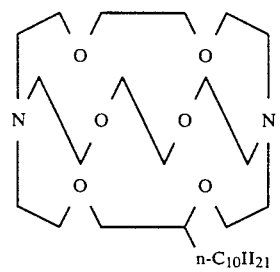
(X-f)

-continued

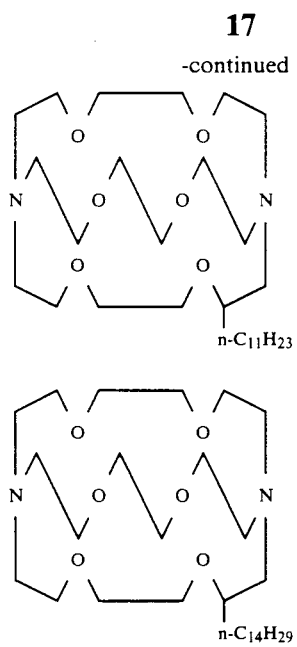

The monocyclic amino ethers are represented by the general formula (XI) and substituted derivatives thereof:

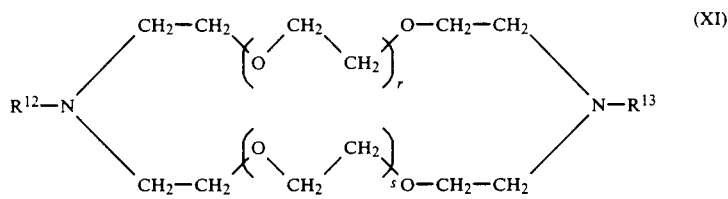

wherein r is 0, 1 or 2; s is 0, 1 or 2; $R^{12}$ and $R^{13}$ each represents H or a substituted or unsubstituted hydrocarbon group having 1 to 80 carbon atoms. Specific examples are shown below:

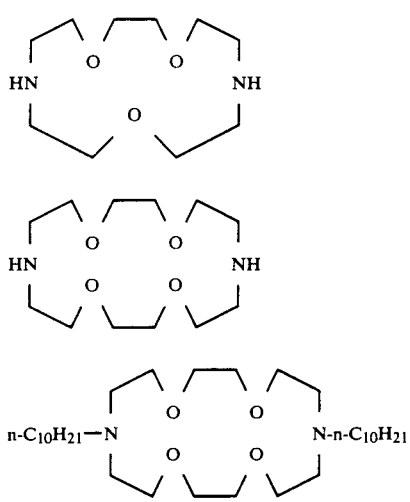

-continued

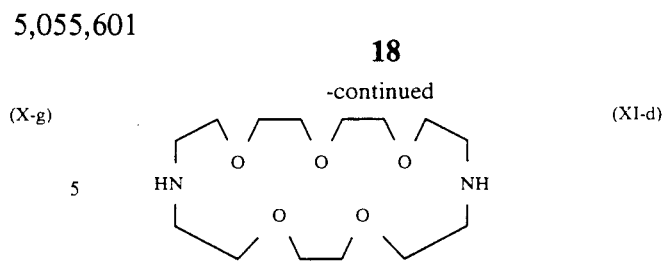

(3) Polyethylene Glycol or Polyethylene Glycol Derivatives

Various kinds of polyethylene glycols are usable but polyethylene glycols having a polymerization degree of not less than 10 are preferred.

The polyethylene glycol derivatives include the compounds represented by the general formula (XII) or (XIII) and their substituted derivatives, copolymers of ethylene oxide and other monomers, and surface active agents containing the polyethylene glycol structure.

$$R^{14}O-CH_2-CH_2-O)_tH \quad (XII)$$

(wherein t is equal to or greater than 5 and $R^{14}$ is a substituted or unsubstituted hydrocarbon group having 1 to 80 carbon atoms.)

$$R^{15}O-CH_2-CH_2-O)_uR^{16} \quad (XIII)$$

(wherein u is equal to or greater than 3 and, $R^{15}$ and $R^{16}$ each represents a substituted or unsubstituted hydrocarbon group having 1 to 80 carbon atoms.)

Specific examples of the polyethylene glycol derivatives represented by the general formula (XII) or (XIII) include the following compounds:

$$\text{n-}C_{16}H_{33}O(CH_2-CH_2-O)_{12}H \quad (XII\text{-a})$$

 (XII-b)

 (XII-c)

$$CH_3O(CH_2-CH_2-O)_{78}CH_3 \quad (XIII\text{-a})$$

$$\text{n-}C_4H_9O(CH_2-CH_2-O)_{10}\text{n-}C_4H_9 \quad (XIII\text{-b})$$

-continued

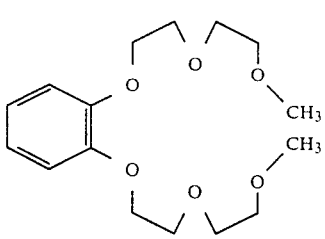
(XII-c)

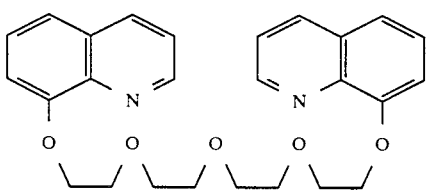
(XIII-d)

Specific examples of copolymers of ethylene oxide and other monomers include ethylene oxide-propylene oxide block copolymers.

Specific examples of the surface active agents containing the polyethylene glycol structure include polyoxyethylene alkylthio ethers, polyoxyethylene alkylamines, polyoxyethylene alkyl ether sulfates, polyoxyethylene alkylphenyl ether sulfates, polyoxyethylene carboxylic acid esters, polyoxyethylene type alkylolamides, polyoxyethylene alkyl ethers, etc.

(4) Polyvinylpyrrolidone or Polyvinylpyrrolidone Derivatives

As the polyvinylpyrrolidone derivatives, there are, for example, copolymers of vinylpyrrolidone and other monomers.

(5) Compounds derived by substituting a part of oxygen atoms in macrocyclic polyethers, macrocyclic aminoethers, polyethylene glycol, polyethylene glycol derivatives and substituted derivatives thereof with a nitrogen atom-containing group, a sulfur atom-containing group or a phosphor atom-containing group, etc.

Examples of these compounds include the following compounds:

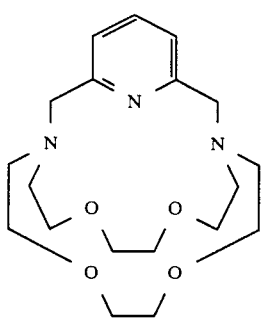
(XIV-a)

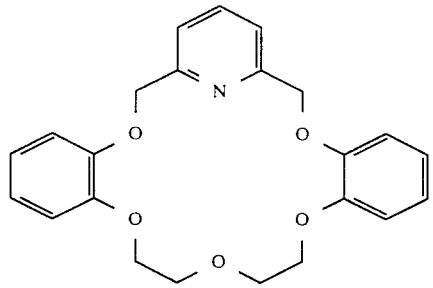
(XIV-b)

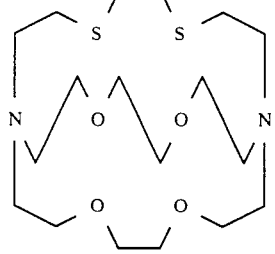
(XIV-c)

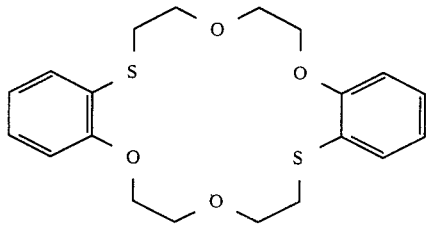
(XIV-d)

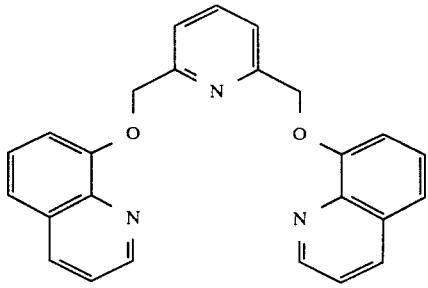
(XIV-e)

Various kinds of the lipophilic complexing agents which can be employed in the process of the present invention have been shown above. However, various other compounds containing a functional group having a coordination capability to metal cations, such as a carbonyl group, a sulfinyl group, a sulfonyl group, a phospholyl group, an ether group, an amino group, an aminoxide group, a pyridine ring, an imidazole ring, a furan ring, etc. can be employed and the lipophilic complexing agents are not limited only to the exemplified compounds. Further, these lipophilic complexing agents may also be those supported on high molecular weight substances or various insoluble carriers by means of various supported methods including covalent bond.

The amount of the catalyst used in the process of the present invention is appropriately chosen depending upon the structure of the catalyst, the kind of solvent, the reaction temperature, the reaction rate required, etc. but generally chosen from the range of 0.0001 mol to 10 mols, preferably 0.001 mol to 1 mol, more preferably 0.001 mol to 0.1 mol, per 1 gram equivalent of hypochlorite ions. When the amount of the catalyst is too small, a substantial reaction rate cannot be obtained; when the amount of the catalyst is excessive, the reaction rate is overly fast so that the reaction rate is controlled only with difficulty. Further, the costs of the catalyst becomes heavy, which is not desirable from an economical point of view.

The reaction of the present invention is carried out in a two phase system of an aqueous phase and an organic phase. It is sufficient that the organic phase as used herein forms a phase containing the fluoro-olefin, different from the aqueous phase, but is not limited beyond that. For example, the organic phase can be a phase mainly composed of the fluoro-olefin per se or can be a phase composed of a catalyst sparingly soluble in water and the fluoro-olefin or, can be a phase composed of the fluoro-olefin and an inert solvent which is substantially immiscible or sparingly miscible in the aqueous phase.

In carrying out the process of the present invention, it is sufficient that an organic phase containing substantially most of the fluoro-olefin and an aqueous phase containing the hypochlorite be present. In addition to these phases, other phases may also be present. For example, even when the organic phase is composed of two media having low compability to form two phases or even when the catalyst is carried on an insoluble carrier to form a third phase, the process of the present invention can be carried out.

As organic solvents for the organic phase which is employed in the process of the present invention, inert solvents which are substantially immiscible or sparingly miscible with the aqueous phase are employed. Specific examples of the organic solvents include aliphatic hydrocarbons such as n-hexane, n-octane, n-decane, etc.; alicyclic hydrocarbons such as cyclohexane, methylcyclohexane, decalin, etc.; aromatic hydrocarbons such as benzene, toluene, xylene, etc.; ethers such as diisopropyl ether, di-n-butyl ether, etc.; chlorinated hydrocarbons such as methylene chloride, chloroform, carbon tetrachloride, 1,2-dichloroethane, chlorobenzene, etc.; chlorofluorocarbons such as 1,2-dichloro-1,1,2,2-tetrafluoroethane, fluorotrichloromethane, 1,1,2-trichloro-1,2,2-trifluoroethane, 1,1,2,2-tetrachloro-1,2-difluoroethane, etc.; perfluorocarbons such as perfluorocyclobutane, perfluorodimethylcyclobutane, perfluorohexane, perfluorooctane, perfluorodecane, hexafluorobenzene, etc.; or solvent mixtures thereof, but the organic solvents are not limited thereto. Upon the choice of organic solvents, appropriate organic solvents are chosen, taking into account the solubility of the fluoro-olefin or the fluoroepoxide, the solubility of the catalyst used in the reaction, the phase separation capability from the aqueous phase, the reaction conditions such as reaction pressure, reaction temperature or the like, etc. Of these various solvents described above, fluorine-containing compounds such as chlorofluorocarbons, perfluorocarbons, etc. are preferred for the process of the present invention since they have high solubility to the fluoro-olefin and the fluoroepoxide and have low miscibility with water. Further, chlorinated hydrocarbons are suited for the process of the present invention since they generally have high solubility to the catalyst.

The volume ratio of the organic phase and the aqueous phase can be freely selected depending upon the type of reactions, the reaction conditions, etc. but it is generally desired that the organic phase be 0.05 time to 20 times, particularly preferably 0.2 time to 5 times, that of the aqueous phase.

The reaction temperature at which the present invention is carried out is determined depending upon the amount of the catalyst, the composition of reaction liquid, the reaction rate required, etc. but generally in the range from $-25°$ C. to $80°$ C., preferably $-20°$ C. to $60°$ C., particularly preferably $-18°$ C. to $40°$ C. When the reaction temperature is too low, a substantial reaction rate is not obtained and, depending upon the situation, the aqueous phase is frozen to make the reaction impossible. Further when the reaction temperature is too high, the fluoroepoxide is seriously decomposed and the selectivity of the fluoroepoxide is decreased.

The reaction pressure under which the present invention is carried out is not overly limited as long as it is sufficient to maintain the organic phase containing the fluoro-olefin and the fluoroepoxide in a liquid phase. Accordingly, the reaction pressure is chosen depending upon the kind and composition of the organic phase but it is generally desired that the pressure be in the range of 1 atm to 20 atms and preferably in the range of 1 atm to 8 atms.

The two phase system reaction of the present invention may be any of reaction systems of a batch process, a semiflow process and a flow process.

Hereafter the present invention will be described in more detail with reference to the examples and comparative examples but is not deemed to be limited thereto.

EXAMPLE 1

In a 50-ml pressure bottle in which a stirrer coated with a fluororesin was incorporated were charged 18 ml of 1,1,2-trichloro-1,2,2-trifluoroethane (hereafter referred to as "F-113"), 30 ml of a sodium hypochlorite aqueous solution having a 12% available chlorine content and containing 1.0 g of sodium hydroxide, 3.5 g (10 mmol) of perfluoro-1-heptene and 0.24 g (0.6 mmol) of tri-n-octylmethylammonium chloride (hereafter referred to as "TOMAC") as the catalyst. After the reaction liquid was cooled to $-10°$ C., the stirrer in the reaction flask was rotated by a magnetic stirrer to mix the reaction liquid, whereby the reaction was initiated. The reaction temperature was kept at $-10°$ C. during the reaction. The rotation of the stirrer was discontinued 2 hours later. The reaction mixture was settled and the aqueous phase and the F-113 phase were allowed to separate. Quantitative assay of perfluoro-1-heptene and 1,2-epoxyperfluoroheptane contained in the F-113 phase by gas chromatography showed that the conversion of perfluoro-1-heptene was 99% and the selectivity of 1,2-epoxyperfluoroheptane was 92%.

COMPARATIVE EXAMPLE 1

The reaction was carried out in a manner similar to Example 1 except that the catalyst TOMAC was not used. As a result, the formation of 1,2-epoxyperfluoroheptane was in a trace amount

EXAMPLE 2

The reaction was carried out in a manner similar to Example 1 except that 20 ml of an aqueous solution containing 4.6 g of high grade bleaching powder (main ingredient: calcium hypochlorite) having an available chlorine content of 65% was employed and the reaction time was 3 hours.

The conversion of perfluoro-1-heptene was 99% and the selectivity of 1,2-epoxyperfluoroheptane was 91%.

EXAMPLES 3 TO 7

The reaction was performed in a manner similar to Example 1 except that 0.24 g of various onium salts were employed in place of the TOMAC, respectively. The results are shown in Table 1.

TABLE 1

| Example | Catalyst | Reaction Time (hr) | Perfluoro-1-heptene Conversion (%) | 1,2-Epoxy-perfluoroheptane Selectivity (%) |
|---|---|---|---|---|
| 3 | (n-Bu)$_4$NCl | 4 | 99 | 87 |
| 4 | (n-Bu)$_4$NHSO$_4$ | 3 | 98 | 89 |
| 5 | (PhCH$_2$)Me$_3$NCl | 3 | 98 | 87 |
| 6 | (n-Bu)$_4$PBr | 3 | 98 | 87 |
| 7 | Ph$_4$AsCl.HCl | 3 | 97 | 86 |

EXAMPLES 8 TO 11

The reaction was performed in a manner similar to Example 1 except that chloroform was employed in place of the F-113 and various polyethers were employed as catalysts.

The results are shown in Table 2.

TABLE 2

| Example | Catalyst | Amount of Catalyst (g) | Reaction Time (hr) | Perfluoro-1-heptene Conversion (%) | 1,2-Epoxy-perfluoroheptane Selectivity (%) |
|---|---|---|---|---|---|
| 8 | 18-crown-6 *1 | 0.20 | 3 | 97 | 88 |
| 9 | Benzo-15-crown-5 *2 | 0.50 | 3 | 99 | 88 |
| 10 | Cryptofix-221 *3 | 0.20 | 3 | 97 | 86 |
| 11 | Cryptofix-22DD *4 | 0.20 | 5 | 98 | 90 |

[Note]

*1 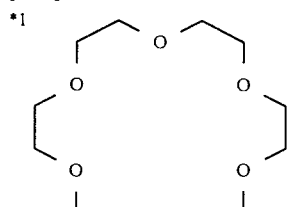

*2 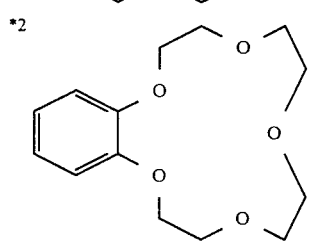

*3 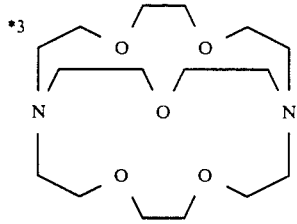

*4 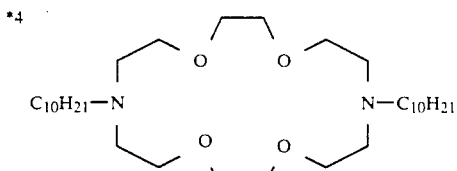

*1, *2: According to the nomenclature by Pedersen (J. Am. Chem. Soc., 89, 7017 (1967))
*3, *4: trademarks by Merck Inc.

EXAMPLE 12

The reaction was carried out for 5 hours in a manner similar to Example 1 except that 0.24 g of a nonionic surfactant, polyoxyethylene oleyl ether, (manufactured by Nippon Oils and Fats Co., Ltd., H.L.B. 16.6), was used as a catalyst. The results indicated that the conversion of perfluoro-1-heptene was 98% and the selectivity of 1,2-epoxyperfluoroheptane was 86%.

EXAMPLE 13

The reaction was carried out for 5 hours in a manner similar to Example 8 except that 0.50 g of polyvinylpyrrolidone (average molecular weight, 40,000) was used as a catalyst. The results indicated that the conversion of perfluoro-1-heptene was 97% and the selectivity of 1,2-epoxyperfluoroheptane was 87%.

EXAMPLE 14

The reaction was carried out in a manner similar to Example 1 except that 2.0 g (10 mmols) of perfluoro-2-butene was used in place of the perfluoro-1-heptene. As a result, the conversion of perfluoro-2-butene was 99% and the selectivity of 2,3-epoxyperfluorobutane was 94%.

EXAMPLE 15

The reaction was carried out in a manner similar to Example 1 except that 2.12 g (10 mmols) of perfluorocyclopentene was used in place of the perfluoro-1-heptene. As a result, the conversion of perfluorocyclopentene was 98% and the selectivity of perfluoro-1,2-epoxycyclopentane was 94%.

EXAMPLE 16

The reaction was carried out in a manner similar to Example 1 except that 3.33 g (10 mmols) of 5,6-dichloroperfluoro-1-hexene was used in place of the perfluoro-1-heptene. As a result, the conversion of 5,6-dichloroperfluoro-1-hexene was 99% and the selectivity of 1,2-epoxy-5,6-dichloroperfluorohexane was 87%.

EXAMPLE 17

The reaction was carried out in a manner similar to Example 1 except that 3.44 g (10 mmols) of ω-hydroperfluoro-1-octene was used in place of the perfluoro-1-heptene. As a result, the conversion of ω-hydroperfluoro-1-octene was 99% and the selectivity of 1,2-epoxy-ω-hydroperfluorooctane was 87%.

EXAMPLE 18

The reaction was carried out in a manner similar to Example 1 except that 2.62 g (10 mmols) of perfluoro-1,5-hexadiene was used in place of the perfluoro-1-heptene. As a result, the conversion of perfluoro-1,5-hexadiene was 98% and the selectivity of 1,2-epoxyperfluoro-5-hexene was 21%.

EXAMPLE 19

The reaction was carried out in a manner similar to Example 1 except that 5.22 g (10 mmols) of 7,8-dibromoperfluoro-1-octene was used in place of the perfluoro-1-heptene. As a result, the conversion of 7,8-dibromoperfluoro-1-octene was 98% and the selectivity of 1,2-epoxy-7,8-dibromoperfluorooctane was 85%.

EXAMPLE 20

The reaction was carried out in a manner similar to Example 1 except that 4.22 g (10 mmols) of 5,6-dibromoperfluoro-1-hexene was used in place of the perfluoro-1-heptene. As a result, the conversion of 5,6-dibromoperfluoro-1-hexene was 98% and the selectivity of 1,2-epoxy-5,6-dibromoperfluorohexane was 86%.

EXAMPLE 21

A reaction similar to Example 1 was carried out in a 1/10 scale that in Example 1 except that heptafluoro-4-pentenenitrile was used in place of the perfluoro-1-heptene. After the reaction was carried out for 15 minutes, the reaction product was analyzed by IR spectrum and GC-MS spectrum. It was confirmed that the epoxide was formed.

EXAMPLE 22

In a 50-ml pressure bottle in which a stirrer coated with a fluororesin was incorporated were charged 18 ml of chloroform, 40 ml of a sodium hypochlorite aqueous solution having a 12% available chlorine content, 3.5 g (10 mmols) of perfluoro-1-heptene and 0.12 g (0.42 mmol) of di-n-butylmethylsulfonium iodide. After the reaction liquid was cooled to $-10°$ C., the stirrer in the reaction flask was rotated by a magnetic stirrer to mix the reaction liquid, whereby the reaction was initiated. The reaction temperature was kept at $-10°$ C. during the reaction. The rotation of the stirrer was discontinued 1 hour later. The reaction mixture was settled and the aqueous phase and the chloroform phase were allowed to separate. Quantitative assay of perfluoro-1-heptene and 1,2-epoxyperfluoroheptane contained in the chloroform phase by gas chromatography showed that the conversion of perfluoro-1-heptene was 99% and the selectivity of 1,2-epoxyperfluoroheptane was 83%.

EXAMPLE 23

The reaction was carried out for 1 hour in a manner similar to Example 22 except that 0.30 g of methyldioctadecylsulfonium iodide was used in place of the di-n-butylmethylsulfonium iodide. The results indicated that the conversion of perfluoro-1-heptene was 98% and the selectivity of 1,2-epoxyperfluoroheptane was 85%.

EXAMPLE 24

The reaction was carried out for 3 hours in a manner similar to Example 22 except that 0.30 g of tris(N,N-diethylamino)sulfonium chloride was used in place of the di-n-butylmethylsulfonium iodide and 18 ml of m-xylene was employed in place of the chloroform. The results indicated that the conversion of perfluoro-1-heptene was 96% and the selectivity of 1,2-epoxyperfluoroheptane was 89%.

EXAMPLE 25

The reaction was carried out in a manner similar to Example 22 except that 2.12 g (10 mmols) of perfluorocyclopentene was used in place of the perfluoro-1-heptene. As a result, the conversion of perfluorocyclopentene was 99% and the selectivity of perfluoro-1,2-epoxycyclopentane was 94%

EXAMPLE 26

Synthesis of 3-Iodopentafluoro-1,2-epoxypropane

In a 1000-ml flask equipped with a stirring apparatus and a thermometer were charged 100 ml of m-xylene, 500 ml of a sodium hypochlorite aqueous solution having a 12% available chlorine content and containing 5.0 g of sodium hydroxide, 20.0 g (77.5 mmols) of 3-iodopentafluoropropene and 0.25 g (0.6 mmol) of TOMAC as a catalyst. After the reaction liquid was cooled to $-10°$ C., the reaction liquid was stirred with the stirring apparatus to initiate the reaction. The reaction was continued while maitaining the reaction temperature at $-10°$ C. After the 15 minutes of reaction time lapsed, the conversion of 3-iodopentafluoropropene became almost 100%. Then the reaction liquid was cooled to $-30°$ C. to freeze the aqueous phase, and the organic phase was separated therefrom. After the organic phase was dried over anhydrous sodium sulfate, the product was isolated from the organic phase through fractional distillation twice. Thus, 8.7 g (yield, 41%) of the captioned compound having a boiling point of 52° C. was obtained.

The analytical data of the thus obtained compound are shown below:

IR Spectrum (gas): 1540 cm$^{-1}$

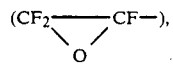

1270 cm$^{-1}$, 1170 cm$^{-1}$, 1140 cm$^{-1}$, 1070 cm$^{-1}$, 1040 cm$^{-1}$, 865 cm$^{-1}$, 695 cm$^{-1}$

Mass Spectrum:
274 (M+), 177 ((CF$_2$I)+), 147 ((M-I)+), 127 (I+), 97 ((C$_2$F$_3$O)+), 50 ((CF$_2$)+)

$^{19}$F-NMR: (solvent: acetone, internal standard: hexafluoro benzene)

| | |
|---|---|
| 16.1 ppm | (multiplet, 1F) |
| 52.8 ppm | (multiplet, 2F) |
| 88.4 ppm | (multiplet, 2F) |

REFERENCE REACTION 1

A 10-ml flask was charged with 1.0 g (3.6 mmols) of 3-iodopentafluoro-1,2-epoxypropane,

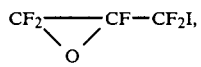

and 2.0 g of tri-n-octylamine at $-10°$ C. in an argon atmosphere. The mixture was reacted at $-10°$ C. for 5 minutes with stirring. The conversion of

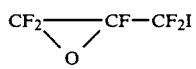

was almost 100%.

The reaction product was isolated from the reaction mixture using a Kugelrore micro distillation apparatus to obtain 0.68 g of

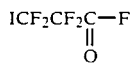

(IR characteristic absorption band: 1880 cm$^{-1}$ (gas)).

In a manner similar to French Patent 1,410,444, the compound

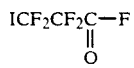

can be converted to $ICF_2CF_2CF_2OCF=CF_2$ useful as a cross linking site monomer by the reaction with hexafluoropropylene oxide followed by the thermal decomposition of the resulting $ICF_2CF_2CF_2OCF(CF_3)COF$.

EXAMPLE 27

Synthesis of Perfluoro-1,2-epoxy-5-trifluoromethyl-4-oxahexane

In a 500-ml flask equipped with a stirring apparatus and a thermometer were charged 100 ml of n-undecane, 150 ml of a sodium hypochlorite aqueous solution having a 12% available chlorine content and containing 4.5 g of sodium hydroxide, 12.6 g (40.0 mmols) of perfluoro-5-trifluoromethyl-4-oxahexene-1 and 1.8 g (4.5 mmols) of TOMAC as a catalyst. After the reaction liquid was cooled to $-5°$ C., the reaction liquid was stirred with the stirring apparatus to initiate the reaction. The reaction was continued while maintaining the reaction temperature at $-5°$ C. After 1 hour of reaction time lapsed, the conversion of perfluoro-5-trifluoromethyl-4-oxahexene-1 became almost 100%. Then, the reaction liquid was cooled to $-30°$ C. to freeze the aqueous phase, and the organic phase was separated therefrom. After the organic phase was dried over anhydrous sodium sulfate, the product was isolated from the organic phase through fractional distillation twice. Thus, 4.2 g (yield, 32%) of the captioned compound having a boiling point of 53° to 54° C. was obtained.

The analytical data of the thus obtained compound are shown below:
IR Spectrum (gas):
1545 cm$^{-1}$

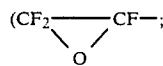

characteristic absorption band), 1260 cm$^{-1}$, 1200 cm$^{-1}$, 1140 cm$^{-1}$, 1010 cm$^{-1}$, 805 cm$^{-1}$, 725 cm$^{-1}$ Mass Spectrum:
313 ((M-F)$^+$), 235 ($CF_2OCF(CF_3)_2$), 169 (($CF(CF_3)_2$)$^+$), 147

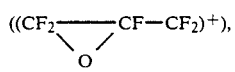

97 (($C_2F_3O$)$^+$), 69 (($CF_3$)$^+$), 50 (($CF_2$)$^+$)

$^{19}$F-NMR: (solvent: acetone, internal standard: hexafluorobenzene)

| 8.0 ppm | (multiplet, 1F) |
|---|---|
| 17.2 ppm | (multiplet, 1F) |
| 47.6 ppm | (multiplet, 2F) |
| 72.9 ppm | (multiplet, 6F) |
| 76.3 ppm | (multiplet, 2F) |

REFERENCE REACTION 2

In a 10-ml flask in which a fluororesin-coated stirrer was incorporated were charged 35 mg of thoroughly dried CsF, 1.0 ml of dry tetraglyme and 2.57 g of perfluoro-1,2-epoxy-5-trifluoromethyl-4-oxahexane in an argon atmosphere. Stirring was performed at $-30°$ C. for 100 hours and then at room temperature for 16 hours to perform a reaction. The conversion of perfluoro-1,2-epoxy-5-trifluoromethyl-4-oxahexane was almost 100%.

The reaction mixture was distilled under reduced pressure and the fractions at 100° C./20 mmHg to 150° C./1 mmHg were collected to obtain 0.92 g of a mixture of a dimer, trimer and tetramer of the epoxide represented by the general formula (V).

REFERENCE REACTION 3

To 10 ml of a 25% aqueous ammonia solution was added 0.80 g of a mixture of the oligomers of perfluoro-1,2-epoxy-5-trifluoromethyl-4-oxahexane obtained in Reference Reaction 2. After the resulting mixture was reacted at room temperature for 1 hour with stirring, the product was isolated and purified to obtain 0.67 g of compounds represented by the formula below:

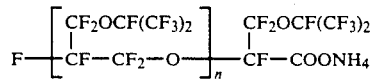

(wherein n is 1, 2 or 3)

The compounds show surface tensions below 20 dye/cm in an aqueous solution and are useful as fluorinated anion surface active agents.

EXAMPLE 28

In a 100-ml flask equipped with a stirring apparatus and a thermometer were charged 10 ml of the organic phase from which the 3-iodopentafluoro-1,2-epxoypropane had been distilled off in Example 26, 50 ml of a sodium hypochlorite aqueous solution having a 12% available chlorine content and containing 0.5 g of sodium hydroxide and 2.00 g (7.75 mmols) of 3-iodopentafluoropropene. The reaction liquid was stirred at $-10°$ C. for 15 minutes. As the result of analysis of the product in the organic phase by gas chromatography, it was found that the conversion of 3-iodopentafluoropropene was 99% and the selectivity of 3-iodopentafluoro-1,2-epoxypropane was 52%

While the invention has been described in detail and with reference to specific embodiment thereof, it will be apparent to one skilled in the art that various changes and modifications can be made therein without departing from the spirit and scope thereof.

What is claimed is:

1. A process for producing a fluoroepoxide from a fluoro-olefin represented by the general formula (I):

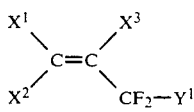

wherein $X^1$, $X^2$, and $X^3$ each is a substituent selected from the group consisting of (a) —F, (b) a perfluoroalkyl group having 2 to 20 carbon atoms and (c) —CF$_2$Y$^1$; Y$^1$ may be the same or different and is a substituent selected from the group consisting of (d) a halogen atom selected from the group consisting of F, Cl, Br and I, (e) —OZ$^1$ and (f) —Z$^1$, wherein Z$^1$ may be the same or different and is a substituted or unsubstituted hydrocarbon group having 20 or less carbon atoms; and $X^1$, $X^2$, $X^3$ and Y$^1$ may combine with one another to form a cyclic compound; provided that all of $X^1$, $X^2$, $X^3$ and Y$_1$ do not represent —F, by using hypochlorite as an oxidizing agent comprising:

epoxidizing the fluoro-olefin in a two-phase system of an aqueous phase and an organic phase which is immiscible in the aqueous phase, said hypochlorite being present in the aqueous phase, in the presence of an inorganic base, at a temperature of between $-20°$ C. and $60°$ C., in the presence of at least one lipophilic catalyst selected from the group consisting of (i) quarternary phosphonium salts, the total number of carbon atoms in quaternary phosphonium ion being not less than 10 per quaternary phosphonium ion, (ii) quanternary arsonium salts, (iii) sulfonium salts, the total number of carbon atoms in sulfonium ion being between 8 to 90 per sulfonium ion, and (iv) lipophilic complexing agents for cations contained in the hypochlorite, to produce a fluoroepoxide in the organic phase.

2. A process for producing a fluoroepoxide as claimed in claim 1, wherein the hypochlorite is dissolved in the aqueous phase.

3. A process for producing a fluoroepoxide as claimed in claim 1, wherein the hypochlorite is suspended in the aqueous phase.

4. A process for producing a fluoroepoxide as claimed in claim 1, wherein the inorganic base is present in an amount of not less than 0.1 gram equivalent per 1 mol of the fluoro-olefin represented by the general formula (I).

5. A process for producing a fluoroepoxide as claimed in claim 5, wherein the inorganic base is sodium hydroxide.

6. A process for producing a fluoroepoxide as claimed in claim 1, wherein the hypochlorite is selected from the group consisting of sodium hypochlorite and calcium hypochlorite.

7. A process for producing a fluoroepoxide as claimed in claim 1, wherein the quaternary phosphonium salts contain quaternary phosphonium ions having 10 to 100 carbon atoms per one quaternary phosphonium ion.

8. A process for producing a fluoroepoxide as claimed in claim 1, wherein the quaternary arsonium salt is selected from the group consisting of a tetraarylarsonium salt and a triarylalkylarsonium salt.

9. A process for producing a fluoroepoxide as claimed in claim 1, wherein the sulfonium salt is represented by the general formula (VIII):

$$R^9R^{10}R^{11}S^{\oplus}Z^{\ominus 2} \quad \text{(VIII)}$$

wherein $R^9$, $R^{10}$ and $R^{11}$, which may be the same or different, each represents a hydrocarbon group or a secondary amino group; the $R^9R^{10}R^{11}S^{\oplus}$ ions may form a heterocyclic ring within the ions; the total carbon atom number contained in $R^9$, $R^{10}$ and $R^{11}$ is in the range of 8 to 90 per one sulfonium ion; and $Z^{\ominus 2}$ represents an organic or inorganic ion.

10. A process for producing a fluoroepoxide as claimed in claim 1, wherein the oxidizing agent is selected from the group consisting of an alkali metal salt of hypochloric acid and an alkaline earth metal (excluding beryllium) salt of hypochloric acid and the catalyst is selected from the group consisting of a lipophilic complexing agent for an alkali metal ion and an alkaline earth metal (excluding beryllium) ion.

11. A process for producing a fluoroepoxide as claimed in claim 10, wherein the lipophilic complexing is a macrocyclic polyether.

12. A process for producing a fluoroepoxide as claimed in claim 10, wherein the lipophilic complexing agent is a macrocyclic aminoether.

13. A process for producing a fluoroepoxide as claimed in claim 10, wherein the lipophilic complexing agent is selected from the group consisting of a polyethylene glycol and a polyethylene glycol derivative.

14. A process for producing a fluoroepoxide as claimed in claim 10, wherein the lipophilic complexing agent is selected from the group consisting of polyvinyl pyrrolidone and a polyvinyl pyrrolidone derivative.

15. A process for producing a fluoroepoxide as claimed in claim 1, further comprising the steps of:
separating the organic phase from the aqueous phase after the epoxidizing step; and
isolating fluoroepoxides from the organic phase.

16. A process for producing a fluoroepoxide as claimed in claim 15, wherein the fluoroepoxide is isolated from the organic phase by means of distillation.

17. A process for producing a fluoroepoxide as claimed in claim 15, wherein the residual organic phase containing the catalyst after the isolating step is re-used as the organic phase of two-phase system in the epoxiding step.

18. A process for producing a fluoroepoxide as claimed in claim 16, wherein the residual organic phase containing the catalyst after the isolating step is re-used as the organic phase of two-phase system in the epoxiding step.

19. A process for producing a fluoroepoxide as claimed in claim 1, wherein the hypochlorite has an available chlorine content in the range of 0.5 to 25% by weight.

20. A process for producing a fluoroepoxide as claimed in claim 19, wherein the hypochlorite has an available chlorine content in the range of 1 to 20% by weight.

21. A process for producing a fluoroepoxide as claimed in claim 1, wherein the ratio of the hypochlorite to the fluoro-olefin is in the range of 0.5 to 30 gram equivalents of hypochlorite ions per 1 mol of fluoro-olefin.

22. A process for producing a fluoroepoxide as claimed in claim 21, wherein the ratio of the hypochlorite to the fluoro-olefin is in the range of 1 to 10 gram equivalents of hypochlorite ions per 1 mol of fluoro-olefin.

23. A process for producing a fluoroepoxide as claimed in claim 22, wherein the phase transfer catalyst is present in an amount in the range of 0.0001 to 10 mols per 1 gram equivalent of hypochlorite ions.

24. A process for producing a fluoroepoxide as claimed in claim 23, wherein the catalyst is present in an amount in the range of 0.001 to 1 mol per 1 gram equivalent of hypochlorite ions.

25. A process for producing a fluoroepoxide as claimed in claim 1, wherein the volumn ratio of the organic phase to the aqueous phase is in the range of 0.05/1 to 20/1.

26. A process for producing a fluoepoxide as claimed in claim 25, wherein the volumn ratio of the organic phase to the aqueous phase is in the range of 0.2/1 to 5/1.

27. A process for producing a fluoroepoxide as claimed in claim 1, wherein the epoxidizing step is carried out at a temperature in the range of $-20°$ C. to $60°$ C. at a pressure in the range of 1 to 20 atmospheres.

28. A process for producing a fluoroepoxide as claimed in claim 27, wherein the epoxidizing step is carried out at a temperature in the range of $-18°$ C. to $40°$ C.

29. A process for producing a fluoroepoxides as claimed in claim 1, wherein the organic phase contains at least one solvent selected from the group consisting of fluorine-containing solvents and chlorinated hydrocarbons.

30. A process for producing a fluoroepoxide as claimed in claim 1, wherein the inorganic base is sodium hydroxide.

31. A process as claimed in claim 1, wherein the lipophilic complexing agent is a large ring polyether.

32. A process as claimed in claim 1, wherein the lipophilic complexing agent is a large ring aminoether.

33. A process as claimed in claim 1, wherein the lipophilic complexing agent is polyethylene glycol or its derivative.

34. A process as claimed in claim 1, wherein the lipophilic complexing agent is polyvinyl pyrrolidone or its derivative.

* * * * *